United States Patent
Garunts et al.

[11] Patent Number: 5,307,235
[45] Date of Patent: Apr. 26, 1994

[54] DEVICE FOR ELECTROACTIVIZATION OF FLUIDS

[75] Inventors: Felix Garunts, Los Angeles, Calif.; Robert Darbinyan, Sundukyanaue, U.S.S.R.

[73] Assignee: Erik M. Arnhem, Los Angeles, Calif.; a part interest

[21] Appl. No.: 856,408

[22] Filed: Mar. 23, 1992

[30] Foreign Application Priority Data

Apr. 16, 1991 [SU] U.S.S.R. .................. 4924102

[51] Int. Cl.$^5$ .......................... B03C 5/02; H01T 19/04
[52] U.S. Cl. ...................................... 361/230; 250/324
[58] Field of Search ............... 422/121; 361/225-231, 361/233; 55/155, 152, 124, 128; 210/748; 250/324-326

[56] References Cited

U.S. PATENT DOCUMENTS

| | | | |
|---|---|---|---|
| 3,898,408 | 8/1975 | Cookson et al. | 55/155 |
| 4,066,526 | 1/1978 | Yeh | 55/152 |
| 4,244,710 | 1/1981 | Burger | 422/121 |
| 4,244,712 | 1/1981 | Tongret | 422/121 |
| 4,357,151 | 11/1982 | Helfritch et al. | 55/124 |
| 4,620,917 | 11/1986 | Nowaza et al. | 210/748 |
| 5,084,072 | 1/1992 | Reynolds | 55/155 |

Primary Examiner—A. D. Pellinen
Assistant Examiner—Richard Elms
Attorney, Agent, or Firm—Erik M. Arnhem

[57] ABSTRACT

An ionizer device for gases or liquids includes a housing that is internally subdivided by an annular tubular partition into a central ionizer chamber and a surrounding overflow chamber. An electron source electrode is located with the ionizer chamber. An annular electron collector electrode is located within the overflow chamber in surrounding relation to the tubular partition. Fluid can be recirculated from the overflow chamber back to the fluid source through an opposite charged neutralizer electrode mechanism designed to replace electrons collected from the fluid by the collector electrode.

9 Claims, 2 Drawing Sheets

DEVICE FOR ELECTROACTIVIZATION OF FLUIDS

BACKGROUND

This invention relates to a device for ionizing fluids. The device may be applied to gases or to liquids.

Ionized air is known to be useful in burners as an oxygen source for improving the combustion process. In one known arrangement the ionized air is produced by feeding raw air into contact with a cathode spaced from anode means in proximity to nozzles used to mix the ionized air with fuel. The cathode can be a pipe electrode, and the anode can be a frame surrounding the pipe electrode.

Ionized water is known to be useful agriculturally as a means for increasing crop yields. Also, ionized water has been used in medicine for the treatment of certain diseases and for the sterilization of medical instruments. Ionized water has also proven useful as a treatment device in the boring of wells in the earth surface.

SUMMARY OF THE INVENTION

The present invention is directed to a device for ionizing fluids, being in constant flowing motion, wherein any fluid that fails to be ionized is recirculated through an overflow chamber and back to the fluid source for passage through the device a second time. The aim is to provide a fluid ionizing device that has relatively high productivity and ionization efficiency.

In one form of the invention the ionizing device comprises a housing that has a porous dielectric tubular partition therein, whereby the space circumscribed by the tubular partition constitutes an ionization chamber, and the space surrounding the tubular partition constitutes an overflow chamber containing electrodes with voltage source plus and minus (+ and −). Fluid that fails to be ionized passes through the porous partition into the overflow chamber for recirculation back to the fluid source; ionized fluid passes from the ionization chamber through a separate outlet.

THE DRAWINGS

DESCRIPTION OF A PREFERRED EMBODIMENT OF THE INVENTION

Figure 1:
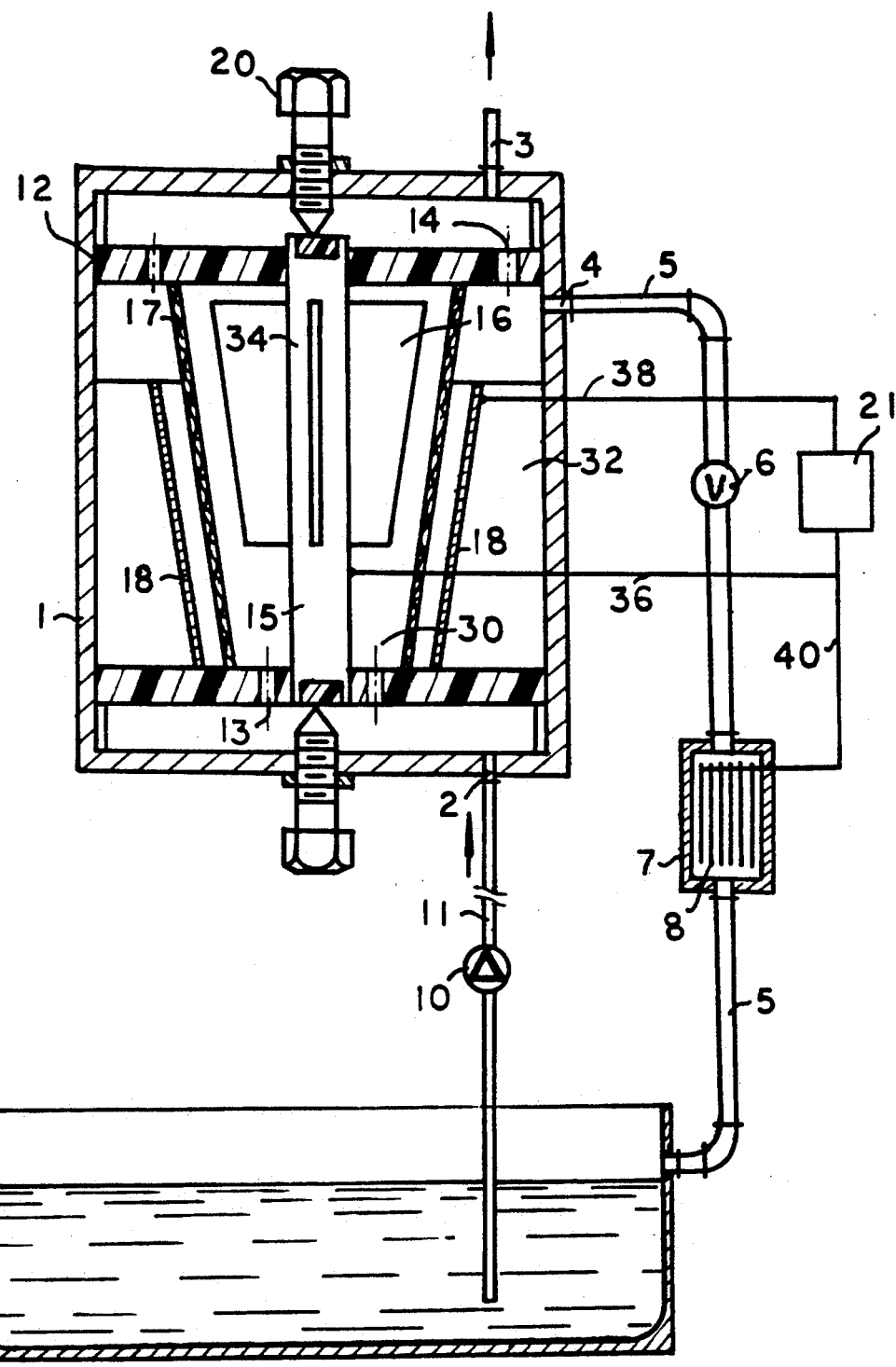
FIG. 1 is a schematic view of a liquid ionization device embodying the invention.

FIG. 1 shows a liquid ionization device that includes a tubular housing 1 having two cross-wise located and spaced dielectric plates 12 therein. A liquid line 11 leads from a supply tank 9 to a liquid inlet 2 on housing 1. A pump 10 supplies the motive force for moving the liquid from the tank through housing 1. Ionized liquid exits from the housing through an outlet pipe 3. The liquid can be water.

Arranged between dielectric plates 12 is an annular tubular electron collector electrode 18. Electrode 18 can be configured as a truncated conical metal sleeve having a large multiplicity of holes or perforations therein. Each perforation can be a circular hole having a diameter of approximately 0.2 to 0.3 inch. The entire length and circumference of the tubular electrode is substantially perforated.

An annular dielectric partition 17 is located between electrodes 15 and 18. Partition 17 can be a heavy porous cotton fabric material attached to sleeve 18. The porous dielectric partition subdivides housing 1 into a central ionization chamber 30 and an annular overflow chamber 32. Pressurized liquid can flow from chamber 30 through the porous partition 17 into chamber 32. Liquid is admitted to chamber 30 through holes 13 in the associated dielectric plate 12; ionized liquid exits from chamber 30 through holes 14.

Arranged within chamber 30 is an electron source electrode 15. As illustratively shown, the electron source electrode comprises a cylindrical support means 34 arranged centrally in chamber 30, and at least three radial plates 16 extending from support means 34 toward the electron collector electrode 18. More than three radial plates can be used if desired or necessary. The outer edges of the plates are sharp to promote electron discharge in the zones near annular partition 17. As shown, the outer edges of plates 16 are parallel to the conical surface of the collector electrode, whereby there is a uniform spacing of the plate edges from the electrode 18 surface along the axial length of the electron source electrode.

Electrodes 15 and 18 are connected to a single voltage source (power supply) 21 through electrical lines 36 and 38. Electrons discharged from plates 16 of the electron source electrode are effective to ionize the liquid flowing from inlet 2 to outlet 3. Some liquid flows from chamber 30 through dielectric partition 17 into chamber 32. Collector electrode 18 removes electrons from the liquid in chamber 32. Partition 17 spaces collector electrode 18 from ionization chamber 30, whereby the electron-collection action of electrode 18 is confined essentially to the liquid in chamber 32.

The liquid in chamber 32 is returned to tank 9 through a return line 5 that contains a charge neutralizer means 7. Neutralizer means 7 comprises a series of negatively charged plates 8. As shown in FIG. 1, plates 8 are connected to power supply 21 via an electrical line 40.

The function of neutralizer means 7 is to neutralize the effect of the electron collector electrode 18. Electrons generated by the negatively charged plates 8 fill the holes produced by collector electrode 18.

The efficiency of the ionizing action of the electron source electrode 15 depends partly on the spacing between the edges of plates 16 and the surface of collector electrode 18. This spacing may be adjusted by adjusting support means 34 longitudinally along the central axis of chamber 30. Various adjustment devices can be utilized for this purpose. As shown in FIG. 1, the adjustment mechanism comprises two adjustment screws 20 having screw connections with housing 1. End support means 34 have semi-elastic plugs therein engageable with the screws, whereby screw movements can be used to shift electrode 15 in a desired direction (up or down in FIG. 1).

Figure 2:
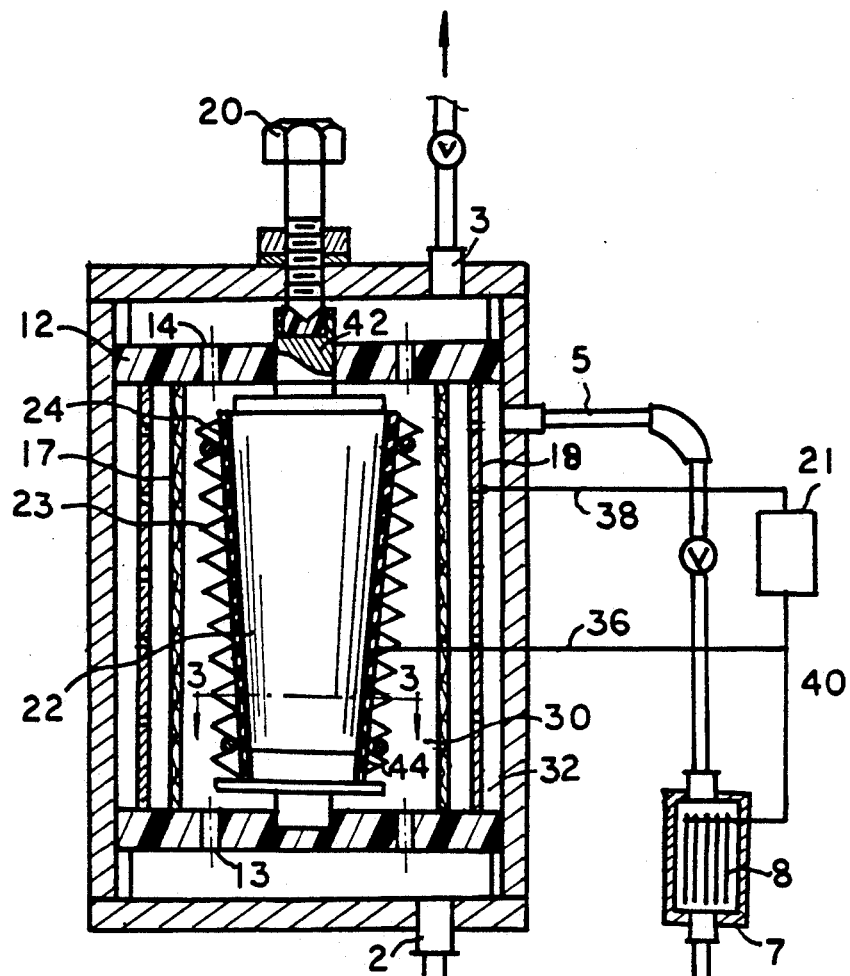
FIG. 2 is a schematic view of a gas ionization device embodying the invention.
Figure 3:
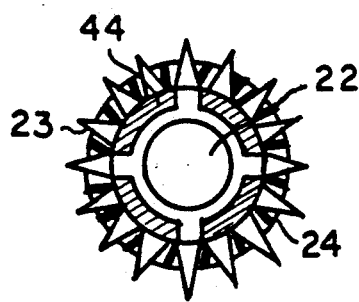
FIG. 3 is a fragmentary sectional view taken on line 3—3 in FIG. 2.

FIGS. 2 and 3 show a second form of the invention adopted to ionize a gas, e.g. air. The air or other gas is supplied by a non-illustrated pump for upflow through the nozzle 26 of an ejector 25. Recirculated air is introduced to the ejector through a gas return line 5a. Flow of air upwardly through nozzle 25 from the nonillustrated source induces a flow of gas from line 5a into the ejector.

In the FIG. 2 arrangement the electron collector 18 is a cylindrical perforated metal sleeve 18. Partition 17 is a perforated dielectric tubular element arranged spatially apart from the inner surface of sleeve 18.

The electron source electrode comprises a metal frusto-conical support element 22 having a stub shaft portion 42 projecting upwardly through the upper dielectric plate 12. At least three segmental wall members 44 extend along the surface of element 22 to mount a large multiplicity of needle electrode elements 23. As shown in FIG. 3, the inner surfaces of wall members 44 are curved to conform with the curved surface of support member 22.

An elastomeric sock 24 extends around and along wall members 44 to retain said members on conical support member 22. Needle elements 23 project through holes in the elastomeric sock. The sock exerts a squeezing force on wall members 44, whereby the wall members exert upward cam forces on conical support member 22 An adjustment screw 20 can be turned to adjust the location of member 22 along its axis. Member 22 exerts a spreader force on wall members 44, whereby the associated needle elements 23 can be adjusted laterally toward or away from collector electrode 18, i.e. normal to the axis of conical support member 22.

In operation of the FIG. 2 device, the ionized gas is discharged from ionizer chamber 30 through outlet pipe 3. Some gas flows into annular chamber 32 through perforated partition 17; such gas is recirculated through a line 5a that contains a charge neutralizer means 7 (similar in function to neutralizer means 7 in FIG. 1).

What is claimed is:

1. A device for ionizing fluids, comprising:
    a housing;
    a porous dielectric partition subdividing said housing into two parts of an ionizing chamber;
    an electron source electrode having a multiplicity of sharpened surfaces to promote electron discharge into a fluid flowing through the ionizing chamber in said ionizing chamber arranged at one of the sides of the dielectric partition;
    an electron collector electrode arranged at the other side of the dielectric partition;
    a fluid inlet duct connected to said ionizing chamber, and means for pumping fluid through said duct;
    a first fluid outlet means connected to said ionizing chamber remoted from said inlet duct so that fluid is required to flow through the ionizing chamber to reach said first fluid outlet means adjacent to the electron source electrode;
    a second fluid outlet means connected to the ionizing chamber part in which the electron collector electrode is arranged;
    a fluid return line operatively connected between said second fluid outlet means and said fluid inlet duct, whereby some of the fluid admitted to said ionizing chamber is recirculated back to the inlet duct;
    neutralizer electrode means in said fluid return line for generating electrons in the recirculating fluid, to thereby neutralize the effect of said collector electrode on the fluid.

2. The device of claim 1, wherein said electron collector electrode is annular and comprises a metal sleeve having perforations extending therealong for flow of fluid from the ionizing chamber toward said second fluid outlet means.

3. The device of claim 2, and further comprising means for adjusting the spacing between the sharpened surfaces on the electron source electrode and the annular collector electrode.

4. The device of claim 2, wherein said electron source electrode comprises a conical support means located centrally in said ionizing chamber, and a large multiplicity of needle electrode elements projecting from said conical support means toward said annular electron collector electrode.

5. The device of claim 1, wherein said electron source electrode comprises a multiplicity of needle electrode elements.

6. The device of claim 4, and further comprising means for adjusting said conical support means in the direction of its axis; said needle electrode elements being slidably mounted on said conical support means so that said needle electrode elements are moved toward or away from said annular electron collector electrode during adjusting movements of said conical support means.

7. The device of claim 6, and further comprising an annular elastic sock means encircling said conical support means for retaining said needle electrode elements on said conical support means.

8. The device of claim 6, wherein said electron source electrode further comprises plural segmental wall members encircling said conical support means, said needle electrode elements being carried by said segmental wall members so as to extend away from said conical support means; and an elastomeric sock means encircling said segmental wall members to hold said wall members against the conical support means.

9. The device of claim 1, and further comprising a single electrical power source in circuit with said electron source electrode, said electron collector electrode, and said neutralizer electrode means.

* * * * *